United States Patent
Coleman et al.

(10) Patent No.: US 6,783,838 B2
(45) Date of Patent: Aug. 31, 2004

(54) COATED FILM LAMINATE HAVING AN IONIC SURFACE

(75) Inventors: Patrick L. Coleman, Minneapolis, MN (US); Kurt J. Halverson, Lake Elmo, MN (US); James I. Hembre, Plymouth, MN (US); Sanjay L. Patil, Minneapolis, MN (US); Anila Prabhu, Woodbury, MN (US); Raj Rajagopal, Woodbury, MN (US); Jerald K. Rasmussen, Stillwater, MN (US); Barbara C. Swenson, North St. Paul, MN (US); Patrick S. Quint, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 42 days.

(21) Appl. No.: 09/845,946

(22) Filed: Apr. 30, 2001

(65) Prior Publication Data

US 2002/0160367 A1 Oct. 31, 2002

(51) Int. Cl.[7] .................................................. B23B 5/00
(52) U.S. Cl. ........................ 428/152; 428/141; 428/174; 428/334; 428/335; 428/500; 436/6; 436/180; 530/810; 530/816
(58) Field of Search .................. 428/141, 152, 428/174, 334, 335, 500, 436, 336; 435/6, 180; 530/810, 816

(56) References Cited

U.S. PATENT DOCUMENTS

| 3,910,819 | A | 10/1975 | Rembaum et al. ............ 195/1.7 |
| 4,451,619 | A | 5/1984 | Heilmann et al. |
| 5,138,026 | A | 8/1992 | Miyasaka et al. ............ 528/328 |
| 5,278,377 | A | 1/1994 | Tsai |
| 5,446,270 | A | 8/1995 | Chamberlain et al. |
| 5,529,708 | A | 6/1996 | Palmgren et al. |
| 5,593,809 | A | * 1/1997 | Kim et al. .................... 430/213 |
| 5,925,455 | A | 7/1999 | Bruzzone et al. |
| 6,319,664 | B1 | 11/2001 | Bookbinder et al. ............ 435/4 |
| 6,329,113 | B1 | * 12/2001 | Bourdelais et al. ............ 430/60 |
| 6,403,278 | B1 | * 6/2002 | Fehervari et al. ............ 430/203 |
| 6,479,222 | B1 | * 11/2002 | Jones et al. .................. 430/350 |
| 2002/0142306 | A1 | * 10/2002 | Coleman et al. ................ 435/6 |
| 2002/0160367 | A1 | * 10/2002 | Coleman et al. ................ 435/6 |
| 2002/0160530 | A1 | * 10/2002 | Coleman et al. ............. 436/518 |
| 2003/0022216 | A1 | * 1/2003 | Mao et al. ....................... 435/6 |
| 2003/0049435 | A1 | * 3/2003 | Haddad et al. .............. 428/328 |
| 2003/0108879 | A1 | * 6/2003 | Klaerner et al. ................ 435/6 |

FOREIGN PATENT DOCUMENTS

| WO | WO 99/53319 | 10/1999 |
| WO | WO 01/16370 | 3/2001 |

* cited by examiner

Primary Examiner—D. Lawrence Tarazano
(74) Attorney, Agent, or Firm—Christopher D. Gram; Robert W. Sprague

(57) ABSTRACT

A coated laminate having an ionic surface including a shrinkable polymeric film, an ionic coating and, optionally, a hydrogel is disclosed. A method for transferring sample molecules from a matrix to a coated laminate having an ionic surface also is disclosed.

37 Claims, 2 Drawing Sheets

COATED FILM LAMINATE HAVING AN IONIC SURFACE

BACKGROUND

Analysis and detection of biological molecules typically involve placing a sample onto an immobilizing membrane and then performing steps to detect the presence of or quantitate one or more particular biological molecules in the sample. A sample may be spotted directly onto the immobilizing membrane or transferred from a matrix to the immobilizing membrane by blotting. Such a transfer may be necessary because the matrix can be unsuited for many of the biological or chemical assays known to those skilled in the art. The transfer may be passive or energy-driven, such as by an electric current. Once the sample has been transferred to the membrane, the desired assay can be performed on the immobilized sample.

Methods of transferring biological molecules to immobilizing membranes are known in the art. For example, polynucleotide sequences may be transferred from a gel made of agarose or polyacrylamide to a cellulose-derived or nylon membrane. Similarly, proteins may be transferred from an SDS-polyacrylamide gel to a cellulose-derived or nylon membrane. Immobilizing membranes made from nylon or cellulose-derived materials are porous and permit the transfer of polynucleotides or proteins through a variety of processes, some of which are energy independent and some of which, such as electroblotting, are energy-driven.

Many assays performed on biological molecules can be performed on a miniaturized scale. Many of these assays use samples and reagents that oftentimes are expensive or difficult to obtain. Accordingly, assays performed on a miniaturized scale are desirable because they may dramatically reduce the amount of sample and reagents required for performing the assay. Miniaturized assays are especially desired when an expensive or limited sample can be concentrated, thereby reducing the amount of the sample required for the assay while simultaneously increasing the sensitivity, accuracy or efficiency of the assay. In addition to the reduction of volume, miniaturization allows hundreds or thousands of assays to be performed simultaneously.

A heat-shrinkable film such as that reported in International Publication No. WO 99/53319, published Oct. 21, 1999, permits samples to be concentrated for miniaturized assays. What is needed is a laminate including a shrinkable film that can be used to immobilize molecules transferred to the laminate for subsequent detection or assay.

SUMMARY

The present invention provides a laminate having an ionic surface that can be used to immobilize sample molecules transferred to the laminate. The laminate includes a shrinkable substrate such as a polyethylene shrink film. The laminate also includes an ionic coating layer. The ionic coating layer may include, for example, one or more ionic polymers, a hydrogel including hydrolyzed azlactone moieties, bifunctional molecules affixed to a hydrogel, or a hydrogel with an overcoating of one or more ionic polymers. The laminate may also include one or mask layers affixed, directly or indirectly to the substrate. Sample molecules may be transferred from a matrix, such as a gel for separating sample molecules, to the laminate by an energy-independent process or by a process that is energy-dependent, such as electroblotting. The ionic surface reversibly affixes desired sample molecules to the laminate. Because the laminate is shrinkable, sample molecules that have been transferred to the laminate may be concentrated for use in a miniaturized assay.

Various other features and advantages of the present invention should become readily apparent with reference to the following detailed description, examples, claims and appended drawings. In several places throughout the specification, guidance is provided through lists of examples. In each instance, the recited list serves only as a representative group and should not be interpreted as an exclusive list.

DEFINITIONS

For purposes of this invention, the following definitions shall have the meanings set forth.

"A" or "an" refers to one or more of the recited elements.

"Affix" shall include any mode of attaching biological molecules to a substrate. Such modes shall include, without limitation, covalent bonding, ionic bonding, and adherence, such as with an adhesive, physical entrapment, and adsorption. This may or may not require the use of linking agents.

"Amphoteric" as used herein shall mean, with respect to any molecule, compound, composition or complex, having character of both an acid and a base. The term includes molecules, compounds, compositions or complexes that are both anionic and cationic, e.g., a polypeptide at its isoelectric point.

"Bifunctional" as used herein shall mean, with respect to any molecule, compound, composition or complex, having more than one functional group. For example, a bifunctional molecule may have an amino group capable of forming a covalent bond with an azlactone moiety and an anionic group capable of forming an ionic bond with a cation.

"Density" shall mean a measure of quantity per unit projected area of a substrate, such as, for example, molecules per square centimeter.

"Heat-relaxable" or "heat-shrinkable" shall mean, in the context of a material such as a substrate, that the material undergoes some relaxation or shrinkage in at least one dimension in response to the transmission of thermal energy into the material.

"Ionic" shall mean any chemical species that has a formal charge, i.e., has an excess (negative formal charge) or a deficiency (positive formal charge) of electrons on at least one atom of the species. A polymeric surface is "ionic" if it contains at least one chemical species having a formal charge even if the polymeric coating is associated with a counterion (e.g., in solution) having an opposite formal charge. The counterion may produce a surface with a net neutral charge even though the polymer surface itself has a formal positive or negative charge.

"Linking agent" shall mean any chemical species capable of affixing a "Molecule" to a substrate. Linking agents can be covalently bonded to the substrate or can be provided by a polymeric coating thereon.

"Molecule" shall be construed broadly to mean any molecule, compound, composition or complex, either naturally occurring or synthesized, that can be detected or measured in or separated from a sample of interest. Molecules include, without limitation, polypeptides, fatty acids, polynucleotides, carbohydrates, polysaccharides, hormones, steroids, lipids, vitamins, bacteria, viruses, pharmaceuticals, and metabolites.

"Polynucleotide" shall mean any polymer of nucleotides without regard to its length. Thus, for example, ribonucleotides and deoxyribonucleotides are each included in the definition of polynucleotide as used herein, whether in single- or double-stranded form. A polynucleotide, as used herein, may be obtained directly from a natural source or may be synthesized using recombinant, enzymatic or chemical techniques. A polynucleotide may be linear or circular in topology and can be, for example, a vector such as an expression vector, cloning vector or any type of plasmid, or any fragment thereof.

"Polypeptide" shall mean any polymer of amino acids without regard to its length. Thus, for example, the terms peptide, oligopeptide, protein, enzyme, and fragments thereof are all included within the definition of polypeptide as used herein. The term also includes polypeptides that have been modified by post-translational expression or synthetic processes yielding, for example, glycosylated, acetylated, phosphorylated polypeptides, or peptide nucleic acids. Accordingly, a polypeptide may be obtained directly from a natural source or may be synthesized using enzymatic or chemical techniques.

"Polysaccharide" shall mean any polymer of saccharides without regard to its size. The term also includes classes of molecules that are polymers of saccharides in combination with other monomers such as amino acids, nucleotides, and any polymers thereof. Such classes of molecules include, but are not limited to, glycosaminoglycans, proteoglycans and glycolipids.

"Projected surface area" shall mean the surface area for a surface as is calculated with respect to the plane encompassing the "x" and "y" axes of the surface.

"Recoverable" means, in the context of a material, such as a substrate, that the material is stretched and capable of subsequently recovering at least one dimension, preferably to substantially its original size.

"Relaxable" shall mean, in the context of a material such as a substrate, that the material is capable of relaxing or shrinking, in at least one dimension. Preferably, shrinkage occurs by at least about 10%.

"Shrinkable," "shrinking" or "shrunk" shall mean, in the context of a material such as a substrate, that the material is capable of being, is, or has been decreased in its length in at least one dimension, whether by recovery, relaxation, or any other means.

"Topographical surface area" shall mean the area of a surface as calculated with respect to the planes encompassing the "x", "y" and "z" axes of the surface.

"Undulations" or "undulated" shall mean convoluted, wave-like forms. For purposes of this invention, it is preferred that an undulated surface includes undulations that do not form a regular pattern. "Undulations" or "undulated" does not include structures such as reservoirs or microwells that are created by methods such as for example printing, embossing, casting, molding, laserscribing, photolithography, etching, mechanical scratching, or scoring.

DETAILED DESCRIPTION OF THE INVENTION

The present invention provides a laminate having an ionic surface that can be used to immobilize sample molecules that have been transferred to the laminate. The laminate includes a shrinkable substrate such as a polyethylene shrink film. The laminate also includes an ionic coating layer. The coating layer may include, for example, one or more ionic polymers, a hydrogel including hydrolyzed azlactone moieties, bifunctional molecules affixed to a hydrogel, or a hydrogel with an overcoating of one or more ionic polymers. Because the laminate is shrinkable, sample molecules that have been transferred to the laminate may be concentrated for use in a miniaturized assay. The sample molecules may be transferred to the laminate by any process such as spotting, passive blotting or electrophoretic transfer, namely electroblotting, although these are not necessarily the only possible transfer processes. The ionic surface may reversibly affix desired sample molecules to the laminate. Because the laminate is shrinkable, sample molecules that have been transferred to the laminate may be concentrated for use in a miniaturized assay.

The Laminate

Figure 1A:
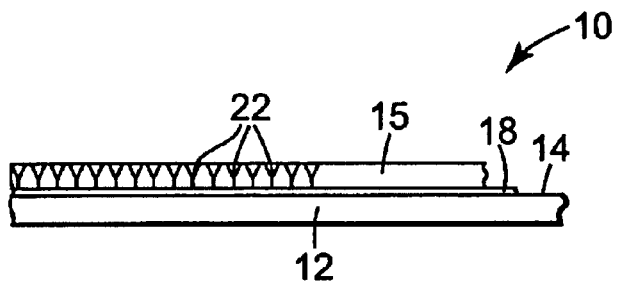
FIG. 1a is a side view of one embodiment of the laminate of present invention prior to relaxation of the substrate thereof.
Figure 1B:
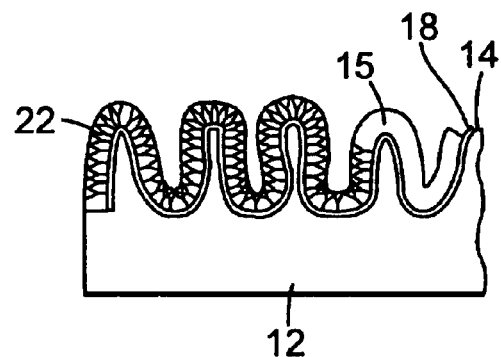
FIG. 1b is a side view of the laminate of FIG. 1a subsequent to relaxation of the substrate thereof.

With reference to FIGS. 1a and 1b, the laminate 10 generally includes a substrate 12 with at least one major surface 14 having a surface area. The major surface 14 may be generally smooth or may include undulations. The substrate 12 may be any number of shapes. The shape of the substrate 12 is not limiting, so long as the substrate 12 provides a base for applying a surface coating 15 or optional layer 18 thereon, as described more fully below.

The substrate 12 is a shrinkable, polymeric material. Accordingly, the substrate 12 has a projected surface area and a topographical surface area. Prior to shrinking, the projected surface area and the topographical surface area are substantially equivalent. When shrunk, however, the surface of the substrate 12 may become undulated. In this case, the topographical surface area will be greater than the projected surface area.

A surface coating 15 is at least partially adhered, directly or indirectly, to the substrate 12 and has a generally smooth appearance, shown in Figure 1a. The surface coating 15 has a projected surface area and a topographical surface area. Accordingly, the projected surface area and the topographical surface area of the surface coating 15 are substantially equivalent prior to shrinking the substrate 12. As described more fully below, upon shrinking of the substrate 12, the topographical surface area of the surface coating 15 becomes greater than the projected surface area of the surface coating 15. The laminate 10 includes a surface coating 15 that is capable of exhibiting a topographical surface area that greatly exceeds the projected surface area. The topographical surface area of the surface coating 15 may be at least about five times greater than the projected surface area. In one embodiment, the topographical surface area is at least fifteen times greater than the projected surface area.

Upon shrinking of the substrate 12, the surface coating 15 may become undulated as depicted in FIG. 1b. While the undulations generally are irregular with respect to any discernable pattern, a regular pattern of undulations may be obtained. The adhesion of the surface coating 15 to the substrate 12 should be sufficient to prevent its total delamination from the substrate 12. When the laminate 10 has an undulated surface, a degree of delamination may actually occur and still provide a useful laminate for use in the claimed method. However, the degree of delamination should not be so great as to interfere with assays being conducted on the laminate 10 or result in effective loss of the surface coating 15 from the substrate 12.

The laminate 10 is capable of exhibiting high topographical surface areas. The high topographical surface area offers opportunities for increasing the signal strength of certain assays. When shrunk, the undulated surface permits more molecules to be concentrated in a given projected surface area compared to transferring molecules to a relatively flat, unshrinkable surface. Also, in the case where transferred molecules are affixed prior to shrinking the substrate 12, the spatial relationship of the affixed molecules to one another on the surface is fixed. Upon shrinking of the substrate 12, the surface of the surface coating 15 becomes undulated, in effect increasing the density of affixed molecules with respect to the projected surface area but substantially maintaining their relative separation due to the topographical surface area of the surface coating 15. This spacing allows presentation of a high density of molecules at or near the surface of the surface coating 15 while minimizing potential steric crowding. This, in turn, facilitates rapid interaction kinetics with prospective assay reagents.

Substrates

The substrate 12 of the laminate 10 is a polymeric material. The material of the substrate 12 is selected with regard to the application for the resulting laminate. For example, if fluorescence will be used to detect the transferred sample molecules, the material used for the substrate 12 may be selected to exhibit low background fluorescence. Also, the substrate 12 material can be selected so that it is compatible with the reagents and conditions of the assays, such as temperature, solvents, and pH.

Many polymeric materials may be suitable for use in the laminate 10. For certain embodiments having a high topographical surface area, one skilled in the art can select materials capable of being oriented, i.e., films that shrink at least in one direction within the film plane when energy such as heat is applied to the film for a specified period of time. Elastomeric materials are also suitable for use as a substrate 12 in the laminate 10. Elastomeric materials include materials that are stretched in at least one direction prior to coating, constrained in the stretched state during coating, and then allowed to recover, thereby reducing the projected surface area of the substrate surface from the stretched state. Thus, herein, a relaxable substrate includes an oriented film and a recoverable substrate includes an elastomeric material.

With respect to oriented films, relaxation need not be equal in any two orthogonal directions within the film plane. In one embodiment, relaxation of the substrate 12, and therefore the laminate 10, is substantially uniform. In this embodiment, the oriented film relaxes in substantially the same amount in each direction, regardless of position on the film plane. If the oriented film employed does not exhibit substantially uniform relaxation characteristics, a registration indicator may be employed to register relative positions on the finished laminate.

The substrate 12 provides a surface 14 upon which additional layers or other films or coatings (e.g., polymeric coatings, mask layers, etc.) may be disposed. Upon relaxation or recovery of the substrate 12, the substrate 12 provides support and integrity to the surface coating 15, or other films or coatings (e.g., polymeric coatings, mask layers, etc.) disposed thereon.

Oriented films suitable for use as a substrate 12 in the laminate 10 include, but are not limited to, biaxially oriented low-density polyethylenes, biaxially oriented linear low-density polyethylenes, and biaxially oriented ultra low-density polyethylenes. Biaxially oriented films exhibit shrinkage in two orthogonal in-plane directions (hereafter referred to as the "x" and "y" directions). Other oriented films that may be suitable for use in the claimed laminate include uniaxially, biaxially, or multiaxially oriented films made by any process known to the art, including, but not limited to: melt-orientation; the blown film, bubble, double-bubble, and tubular processes; length orientation; the process of tentering; extension over a mandrel; thermoforming; and blow molding. Polymers which may be employed in such films include, but are not limited to: polyethylenes, including high density polyethylene, low density polyethylene, linear low density polyethylene, ultra low density polyethylene, and copolymers of ethylene (including ethylene propylene copolymers and ethylene vinyl acetate copolymers); polyolefins, including isotactic polypropylene, syndiotactic polypropylene, and polymethylpentene; polyacetals; polyamides, including polyamide 6 and polyamide 66; polyesters, including polyethylene terephthalate, polybutylene terephthalate, and polyethylene naphthalate; halogenated polymers, including polyvinyl chloride, polyvinylidene chloride, polychlorotrifluoroethylene, polyvinyl fluoride, and polyvinylidene fluoride; styrene polymers, including general purpose polystyrene, syndiotactic polystyrene, and high impact polystyrene; cellulose esters, including cellulose acetate and cellulose propionate; polyketones, including polyetheretherketone and copolymers and terpolymers of carbon monoxide with ethylene and/or propylene; polycarbonates, including the polycarbonate of bisphenol A; phenyl-ring polymers, including polyphenylene sulfide; polysulfones; polyurethanes; polymers of acrylic and methacrylic acids and their esters; ionomers; and copolymers, blends, or layered structures of any of the above-named polymers. Oriented films of any of these polymers may be optionally cross-linked.

Examples of elastomeric materials that may be suitable for use as the substrate 12 in the coated laminate 10 include natural rubber, polyisoprenes, polychloroprene, polyisobutylenes, polybutenes, nitrites, polyurethanes, silicones, random copolymers and terpolymers (such as ethylene-propylene copolymers and ethylene-propylene-diene monomer terpolymers), and block copolymers.

Surface Coating

A surface coating 15 is at least partially adhered, directly or indirectly, to the substrate 12 to form the laminate 10 of the present invention. The surface coating 15 may be indirectly adhered to the substrate 12 through an optional layer 18 that may be desirable for certain applications. The surface coating 15 may be crosslinked. A wide variety of surface coatings 15 may be suitable for use in the present invention. In one embodiment, the surface coating 15 includes an ionic polymer. The polymer may be either cationic or anionic. Suitable materials for providing a cationic polymeric coating 15 include but are not limited to polymers and copolymers made from amine-containing monomers such as 2-vinylpyridine, 3-vinylpyridine, 4-vinylpyridine, (3-acrylamidopropyl)trimethylammonium chloride, 2-diethylaminoethyl acrylate, 2-diethylaminoethyl methacrylate, 3-dimethylaminopropyl acrylate, 3-dimethylaminopropyl methacrylate, 2-aminoethyl methacrylate, dimethylaminoethyl acrylate and methacrylate, 2-acryloxyethyltrimethylammonium chloride, diallyldimethylammonium chloride, 2-methacryloxyethyltrimethylammonium chloride, 3-methacryloxy-2-hydroxypropyltrimethylammonium chloride, 3-aminopropylmethacrylamide, dimethylaminoethyl methacrylamide, dimethylaminopropyl acrylamide, and other similarly substituted acrylamides and methacrylamides; 4-vinylbenzyltrimethylammonium chloride, 4-vinyl-1-methylpyridinium bromide, ethylene imine, lysine, allylamine, vinylamine, nylons and chitosan. Suitable materials for providing an anionic polymeric coating 15 include but are not limited to polymers and copolymers of unsaturated acids such as acrylic, methacrylic, maleic, fumaric, itaconic, vinylbenzoic, N-acryloylamino, or N-methacryloylamino acids; 2-carboxyethyl acrylate; vinyl phosphoric acid; vinyl phosphonic acid; monoacryloxyethyl phosphate; sulfoethyl methacrylate; sulfopropyl methacrylate; 3-sulfopropyldimethyl-3-methacrylamidopropylammonium inner salt; styrenesulfonic acid; 2-acrylamido-2-methyl-1-propanesulfonic acid (AMPS); sulfonated polysaccharides such as heparin, dermatan sulfate, and dextran sulfate; carboxylated polyvinyl chloride; and carboxylated polysaccharides such as iduronic acid, carboxymethylcellulose or alginic acid.

In an alternative embodiment, the surface coating 15 may include a hydrogel. As used herein, a hydrogel means a water-containing gel; that is, a polymer that is hydrophilic and will absorb water, yet is insoluble in water. The hydrogel provides a porous surface coating 15 capable of absorbing, for example, three to five times its dry weight in water. This provides a hydrophilic environment suitable for performing a wide variety of biological, chemical and biochemical assays on the transferred molecules.

In certain embodiments, the surface coating 15 may include linking agents 22 capable of immobilizing or affixing transferred sample molecules, as shown in FIG. 1a. If desired, more than one type of linking agent 22 may be used. When present, linking agents 22 can be an integral component of the coating 15, as depicted in FIG. 1a, or can be affixed in a subsequent step to the surface coating 15, which is disposed on a substrate 12. Any number of processes known in the art may be used to introduce the linking agents 22 to be affixed to the surface coating 15. It is understood that the mode of affixation may vary in accordance with the linking agents 22 employed.

The type of linking agent 22 that may be used in the present invention may vary according to the application and the sample molecule to be detected or quantified. Linking agents 22 suitable for covalent immobilization of transferred sample molecules include azlactone moieties such as those provided by copolymers reported in International Publication No. WO 99/53319, published Oct. 21, 1999. Other useful linking agents 22 are also reported in the same publication. Azlactone moieties are useful because these moieties are suitable for reaction with many different sample molecules, including polypeptides, e.g., proteins. For example, one embodiment of the laminate 10 of the claimed method includes a surface coating 15 of azlactone copolymer forming a hydrogel. Azlactone moieties are hydrolyzed to provide an anionic surface coating 15. Azlactone moieties also generally exhibit high reactivity with transferred molecules or with other coatings comprising different linking agents, such as those described below. Azlactone moieties are also generally hydrolytically stable and therefore have a relatively long shelf life when used in the laminate 10 of the present invention.

Figure 2A:
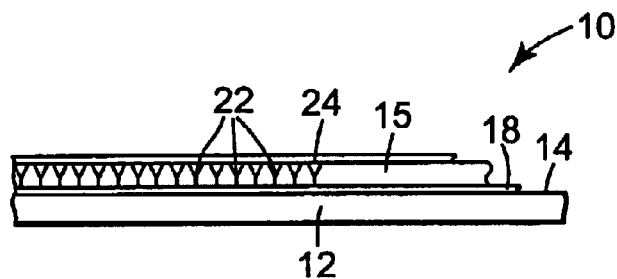
FIG. 2a is a side view of an alternative embodiment of the laminate of the present invention prior to relaxation of the substrate thereof.
Figure 2B:
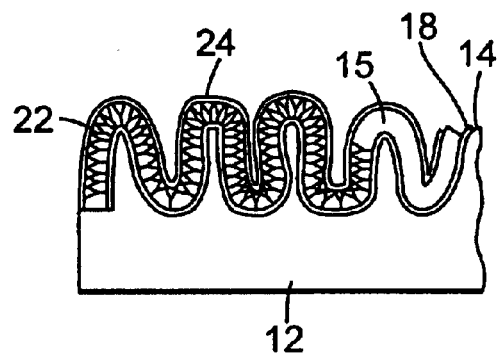
FIG. 2b is a side view of the laminate of FIG. 2a subsequent to relaxation of the substrate thereof.

FIG. 2a shows an alternative embodiment of the laminate 10 of the present invention. An ionic polymeric overcoating 24 is disposed on the surface coating 15 and provides an ionic surface on the laminate 10. The polymeric overcoating 24 may be cationic, anionic or amphoteric. A polymeric overcoating 24 including an ionic surface may be desired to form ionic bonds with desired sample molecules so that the desired sample molecules subsequently can be detected or assayed.

The polymeric overcoating 24 may be used in conjunction with any surface coating 15. For example, a polymeric overcoating 24 may be applied to a surface coating 15 including a hydrogel comprising azlactone copolymers. In such an embodiment, it may be advantageous for the polymeric coating 24 to have functional groups that will covalently react with the azlactone polymer. Alternatively, the polymeric coating 24 may be applied to a surface coating 15 including a non-azlactone, ionic polymer. In such an embodiment, it may be advantageous to have a surface coating 15 and an overcoating 24 of opposite formal charge. In this way, the formal charges on the respective coatings will form ionic bonds between the surface coating 15 and the overcoating 24, thereby decreasing the extent to which the surface coating 15 and the overcoating 24 become delaminated when the resulting laminate 10 is shrunk. Additionally, the laminate 10 of the present invention may include multiple overcoatings 24. The materials described above as being useful for providing a non-azlactone, ionic polymeric surface coating 15 are equally suited for use in an ionic polymeric overcoating 24. Any of these materials may be crosslinked in the polymeric overcoating. The polymeric coating 24 may be selected to provide the specific qualities desired for a particular application. For example, a cationic polymeric overcoating may be selected for an application in which the laminate 10 is designed to affix one or more anionic polypeptides, e.g., proteins.

Figure 3A:
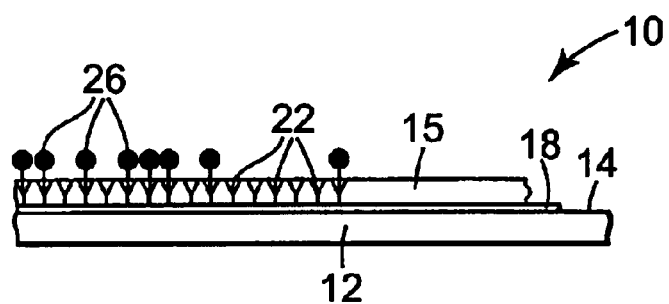
FIG. 3a is a side view of an alternative embodiment of the laminate of the present invention prior to relaxation of the substrate thereof.
Figure 3B:
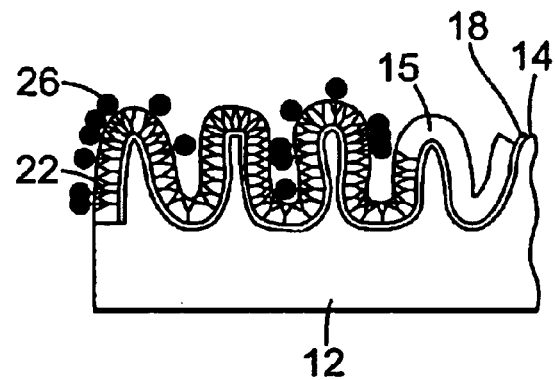
FIG. 3b is a side view of the laminate of FIG. 3a subsequent to relaxation of the substrate thereof.

In yet another embodiment, shown in FIG. 3a, the surface coating 15 may include bifunctional small ionic molecules 26, such as amino-functional ionic molecules, affixed to linking agents 22. In the case of amino-functional ionic molecules, the amine forms a covalent bond with, for example, azlactone moieties in the linking agents 22 of the surface coating 15. The ionic portion of the molecules 26 provides the surface coating 15 with ionic character. The extent of the ionic character is determined by the particular ionic molecules selected for use. In this way, the surface coating 15 is provided with ionic character without requiring a polymeric overcoating. Any ionic molecule also having a functional group that is reactive with any portion of the linking agents 22 may be suitable for the present invention. Suitable amine-functional ionic molecules 26 include, but are not limited to aminocarboxylic acids (e.g., α-, β-, γ-, etc. amino acids such as glycine, alanine, aspartic acid, β-alanine, γ-aminobutyric acid, and 12-aminododecanoic acid); aminosulfonic acids such as 2-aminoethane sulfonic acid (taurine) and 3-amino-1-propanesulfonic acid; aminophosphonic or phosphoric acids such as 2-aminoethanephosphonic acid, 2-aminoethyl dihydrogenphosphate, 2-aminoethyl thiophosphate sodium salt, and aminopropylphosphonic acid; and polyamines such as N,N-dimethylaminoethylamine, N,N-diethylaminopropylamine, N-aminopropylmorpholine, 2-(2-aminoethyl)pyridine, 2-aminoethyltrimethylammonium chloride, diethylenetriamine, triethylenetetraamine, tetraethylenepentaamine, 2-aminoethylpiperidine, and N-(2-aminoethyl)1,3-propanediamine. The ionic molecules 26 may be dispersed randomly over the topographical surface area of the laminate 10 or they may be arranged into a predetermined pattern. The laminate 10 may be designed to have any desired distribution of ionic molecules 26 appropriate for a particular application.

The particular performance characteristics of the laminate 10 with respect to the assay(s) to be performed may be adjusted by varying the thickness of the surface coating 15. For example, fluorescence from a Western blot of transferred albumin and rabbit IgG was greater in laminates having a surface coating thickness of 10,000 Å compared to a laminate having a surface coating of 500 Å. The coating thickness may range from about 100 Å to 50 $\mu$m or more. In some embodiments, the coating thickness may be less than about 30 $\mu$m while other embodiments may have a coating thickness less than about 20 $\mu$m. Thicker coatings may tend to interfere with the shrinking process to some extent. Nevertheless, the surface coating may be designed to have an appropriate thickness to optimize the conditions for a desired assay.

Methods of Relaxation/Recovery and Functionalization

Relaxation and recovery of the films making up the substrate 12 can be accomplished using the methods reported in International Publication No. WO 99/53319, published Oct. 21, 1999. Oriented films exhibit an area shrinkage reduction that is dependent in part on the degree of elongation of the film during orientation thereof. The area shrinkage reduction is a measure of the area shrinkage of the film from its oriented, pre-shrunken dimensions to its dimensions after energy has been applied to shrink the film. For example, a 10 cm×10 cm (100 cm$^2$ area) film that shrinks fifty percent (50%) in the "x" direction and fifty percent (50%) in the "y" direction after the application of sufficient heat will be reduced to 5 cm×5 cm (25 cm$^2$ area), thereby exhibiting an area shrinkage reduction of seventy-five percent (75%). An area shrinkage reduction of about twenty-five percent (25%) is suitable for the laminate 10, but an area shrinkage reduction of more than about seventy-five percent (75%) may be achieved in certain embodiments, thereby producing a laminate with very high-densities of transferred molecules.

When miniaturization is desired, the substrate 12, and therefore the laminate 10, may be shrunk, i.e., a substrate 12 comprising an oriented film may be relaxed or a substrate 12 comprising a stretched elastomeric film may be recovered. The relative positions of the spots or bands occupied by the transferred molecules prior to shrinking the laminate should be maintained after the laminate is shrunk. However, the density of the transferred molecules may be increased dramatically.

With respect to oriented films, the reduction may be effected by the application of heat, although other modes of relaxing oriented films can be used. The mode of size alteration, such as the application of heat, can be selected so that it does not substantially impair the activity of the transferred molecules. For example, fairly high heat may be employed to shrink a substrate 12 having oligonucleotides affixed thereto (approximately 150 degrees Celsius) without destroying the ability to have subsequent DNA hybridization occur with the oligonucleotides.

With respect to elastomeric materials, the reduction of the projected surface area may be achieved by releasing the force that is holding the material in the stretched condition. The substrate 12 may be subsequently treated to hold the substrate 12 in the shrunken format. Alternatively, a backing or other physical means may be applied to the substrate 12 to hold it in the size-altered format.

The relative positions of the transferred molecules are maintained when the laminate 10 of the present invention is shrunk. However, the density of the transferred molecules may be increased dramatically. Accordingly, shrinking the laminate 10 may increase the density of the transferred molecules by a substantial factor. Increases in the density of transferred molecules of 4-fold, 10-fold, and greater than 20-fold are possible according to the claimed method.

Increasing the density of the transferred molecules is advantageous where an intensified detection signal is desired, such as, for example, when fluorescent, absorbent, or chemiluminescent labels are used as detection signals. Moreover, the increase in density of the transferred molecules means that a smaller amount of the sample is required to elicit a signal substantially functionally equivalent, for example, to performing the same assay in a multi-well plate. Additionally, less assay media may be required to perform an assay on the reduced surface area occupied by molecules concentrated on the shrunken laminate 10 according to the present invention compared to performing the same assay, for example, in a multi-well plate or on a non-shrinkable immobilizing membrane.

Additional Optional Features

In certain other embodiments, the laminate 10 may include an optional layer 18. The optional layer 18 may include a mask layer to reduce or prevent transmission of excitation energy through the mask layer to the underlying substrate 12, as reported in International Publication No. WO 01/16370, published Mar. 8, 2001. For other applications, a mask layer may be used to reduce or prevent the transmission of electromagnetic energy from beneath the analyte, e.g., the substrate, that is similar to the electromagnetic signal emitted by the desired analyte in response to the excitation energy. In either case, with a mask layer in place, the electromagnetic signals emitted from the surface of the film can generally be attributed to excitation of the molecule captured on the film rather than the underlying substrate 12 or other portions of the film. As shown in FIG. 1a, certain embodiments will have the optional mask layer 18 underlying the surface coating 15.

The optional layer 18 may alternatively include an electromagnetic energy sensitive material, which may be the same or different than the material of the mask layer, if present. The optional layer 18 including electromagnetic energy sensitive material that is provided on the substrate 12 can take a variety of forms as reported in U.S. patent application Ser. No. 09/459,418, filed on Dec. 9, 1999. Examples of some suitable materials include, but are not limited to, those reported in U.S. Pat. No. 5,278,377 (Tsai); U.S. Pat. No. 5,446,270 (Chamberlain et al.); U.S. Pat. No. 5,529,708 (Palmgren et al.); and U.S. Pat. No. 5,925,455 (Bruzzone et al.). Although the optional layer 18 is depicted as being in direct contact with the substrate 12, one or more intervening layers may be located between the optional layer 18 and substrate 12 provided that the electromagnetic energy sensitive material, if present in the optional layer 18, is in thermal communication with the heat-relaxable material in the substrate 12 such that thermal energy in optional layer 18 is conducted to the substrate 12.

Transfer of Sample Molecules to the Laminate

Sample molecules can be transferred to the laminate 10 by any suitable process. For example, sample molecules may be spotted directly onto a desired area of the laminate 10. Alternatively, sample molecules may be transferred from the matrix to the laminate 10 by passive blotting. The matrix may be, for example, a gel made from agarose or polyacrylamide through which at least one sample molecule has been run. The matrix may or may not separate one or more sample molecules from one another. The matrix is placed in contact with the laminate and the matrix and laminate 10 are assembled into a typical blotting configuration well known in the art, such as between layers of filter paper. Alternatively, the matrix and laminate are assembled in a commercially available blotting apparatus according to the apparatus manufacturer's instructions. During the blotting process, the sample molecules are transferred from the matrix to the laminate 10 in register with their positions in the matrix. Thus, the laminate 10 contains a replica of the pattern of sample molecules that was generated as the sample molecules were run through the matrix.

Alternatively, sample molecules may be transferred from the matrix to the laminate 10 by electroblotting, i.e., blotting driven by an electric current. The matrix and the laminate 10 are assembled in an electroblotting apparatus and the apparatus is run according to the apparatus manufacturer's instructions. Once applied, the electric current drives migration of the sample molecules from the matrix to the laminate 10. As in passive blotting, sample molecules are transferred to the laminate 10 in register with their relative positions in the matrix. Thus, an electroblotted laminate 10 will also contain a replica of the pattern of sample molecules that was generated as the sample molecules were run through the matrix.

Whichever transfer process is used, sample molecules from a single gel may be transferred to more than one laminate 10 as described above. Therefore, one can obtain a series of laminates, each with an identical replica blot of the pattern of sample molecules present in the matrix. The ability to obtain multiple identical blots from one matrix, using the laminate of the present invention, is advantageous for subsequent functional analysis of the transferred sample molecules. For example, one may produce a series of identical blots of a set of separated proteins from a sample comprising a mixture of proteins. One blot might be probed with one or more specific monoclonal antibodies, another one developed for carbohydrate functionality, another for a specific enzyme activity such as phosphatase or phosphorylase, or any of a number of other assays. After evaluating these various assays one would still have the matrix as a source for recovery of the untransferred proteins for further processing.

This is an exceptionally useful application of the present invention as it allows one to perform several different analyses in parallel on replica blots of sample molecules from a single gel. Because each blot is in register with every other blot, individual sample molecules may be identified by their relative positions on each blot and those relative positions will be the same as the relative positions occupied by the sample molecules in the original gel. Thus, results from the series of parallel assays may provide data that can be used, for example, to identify or characterize individual sample molecules in the blots. Once identified or characterized, the position of any of the sample molecule remaining in the original gel is known.

Additionally, because the sample molecules can be concentrated by shrinking the laminate 10 after the sample molecules are transferred, less of the sample molecule may need to be transferred in order to perform the desired assays, thereby preserving more of each of the matrix-bound sample molecules for further processing, if desired. Also, less assay reagent may be needed to perform a particular assay on the transferred sample molecules after they have been concentrated as a result of shrinking the laminate 10, resulting in reduced costs. As an example, proteins from a 2-D protein gel may be transferred to a laminate 10, then shrunk to produce a replica that has, for example, a projected surface area $\frac{1}{20}^{th}$ that of the of the original gel. The shrunken laminate 10 thus may require a smaller volume of reagents to perform a particular assay compared to performing the same assay on proteins transferred to a non-shrinkable immobilizing membrane.

While characterized above with reference to identification and analysis of proteins, the laminate of the present invention may be used with similar advantages with respect to identification and analysis of polynucleotides, polysaccharides or any other class of biological or non-biological molecules. Accordingly, the laminate of the present invention may be used to identify and analyze polynucleotides or polysaccharides in a manner similar to that described above for the transfer, identification and analysis of polypeptides, e.g., proteins.

EXAMPLES

The following examples have been selected merely to further illustrate features, advantages, and other details of the invention. It is to be expressly understood, however, that while the examples serve this purpose, the particular ingredients and amounts used as well as other conditions and details are not to be construed in a matter that would unduly limit the scope of this invention.

Example 1

Preparation of Anionic Coatings

Dye solutions were prepared to assist in the evaluation of ionic coatings. Tryptan Blue (an anionic blue dye, Aldrich Chemical Co.) was dissolved in distilled water at a concentration of 25 mg/25 ml. A Toluidine Blue (a cationic blue dye, Aldrich Chemical Co.) solution was prepared at the same concentration.

A PEI overcoated laminate, prepared as reported in International Application No. WO 01/16370, was challenged with 1 $\mu$l drops of the above dye solutions. After two minutes, the laminate was rinsed with distilled water. A blue-colored stain was produced only where the Tryptan Blue solution had been spotted, indicating that the laminate surface has a cationic formal charge. Longer contact with Tryptan Blue solution led to a deepening of the blue staining. Similar treatment of a laminate having only an azlactone copolymer hydrogel coating produced only a very slight discoloration with either dye, indicating little if any formal charge to the coating.

Another portion of the PEI overcoated laminate was soaked in a solution of 15% wt/wt poly(2-acrylamido-2-methyl-1-propanesulfonic acid) in distilled water for 10 minutes. The film was then rinsed with distilled water and allowed dry, then challenged again with the two dye solutions. This time, only the Toluidine Blue dye stained the film, indicating that the surface of the laminate had been transformed so as to have a formal anionic charge.

Similar treatment of the PEI laminate with a 1% solution of 5000 molecular weight dextran sulfate, sodium salt, produced an new laminate which also stained with Toluidine Blue. Similarly, a solution of heparin transformed the laminate to produce an anionic surface.

A laminate having only an azlactone copolymer hydrogel coating, as reported in International Publication No. WO 99/55319, was immersed in 0.1 N hydrochloric acid for 20 minutes, then rinsed with distilled water and dried. Toluidine Blue dye produced a deep purple stain, while Tryptan Blue produced no stain. Similar treatment of an azlactone laminate with 0.1 N sodium hydroxide, and testing produced a light blue stain with Toluidine Blue.

An azlactone copolymer coated laminate was immersed in 1 M 3-diethylaminopropylamine in distilled water for 20 minutes. The modified laminate was then immersed in dextran sulfate solution as described above, rinsed and dried. Testing with dye solutions produced no stain with Tryptan but a light stain with Toluidine, indicative of an anionic surface charge.

A 1 M solution of taurine was prepared by dissolving 5 grams of taurine in 40 ml of 1 M sodium hydroxide solution. This solution was used to treat an azlactone laminate for 20 minutes. After rinsing and drying, the laminate was found to stain purple with Toluidine but not with Tryptan.

Example 2

Electroblotting of protein onto polyethyleneimine (PEI)-coated shrink film A 1 mg/ml solution of biotinylated bovine albumin (Sigma Chemical Company, St. Louis, Mo.) was prepared in 0.1 M phosphate-buffered saline, pH 7.5, containing 0.1% bovine serum albumin (PBS-BSA). The conjugate contained nine moles of biotin per mole of albumin. Immediately prior to electrophoresis a sample of the biotinylated protein was reduced and denatured with Laemmli reagent (Bio-Rad Corp, Hercules, Calif.) using standard techniques and electrophoresed through a 4–15% acrylamide gradient pre-cast gel (Bio-Rad) at a constant voltage of 100 volts for 45 minutes.

Preparation of dimethylacrylamide/vinylazlactone (DMA-VDM) copolymer coating solutions was accomplished according to Example 10 of International Publication No. WO 99/55319. Solutions were diluted to <5% solids with isopropanol and formulated with enough ethylenediamine added immediately prior to coating to provide 10% crosslinking by weight. Coating was accomplished by use of wire-wound coating rods (Meyer bars). After coating, solvent was removed from the coating by placing the coated film in an oven heated to 50° C. for 30 minutes. Thickness of the dry coating was varied by appropriate choice of coating rod and concentration of the coating solution. Polyethylene shrink film, coated with DMA-VDM was immersed for five minutes in a solution of PEI (Aldrich Chemical Company, Milwaukee, Wis.) diluted to 6% (w/v) with water. The shrink film was removed from the PEI solution, rinsed with water, and allowed to dry.

The gel was subjected to blotting on both nitrocellulose paper and shrink film coated with PEI. The coated shrink film was loaded with the PEI surface facing the gel. Semi-dry blotting was performed using the Bio-Rad semi-dry electrophoretic transfer cell (Model SD Cell) according to the package insert instructions.

The blotted membranes were blocked overnight at room temperature in a buffer of PBS-BSA as described above containing 1.5% additional bovine serum albumin, 1.0% casein (Sigma Chemical Co. St. Louis, Mo.), 0.5% gelatin, and 0.1% TWEEN 20 detergent (Bio-Rad).

A 1:200 dilution of Cy3-labeled mouse monoclonal antibiotin antibody (500 $\mu$g/ml available from Sigma Chemical Co.) was prepared in PBS-BSA. The membranes were incubated in the antibody solution for two hours at room temperature. At the end of the incubation, the membranes were washed three times for five minutes each with a solution of PBS-BSA and 0.1% TWEEN 20 detergent. The membranes were transferred to a dry surface and stored in the dark. They were scanned at 532 nm on GENE PIX 4000 Å array scanner (available from Axon Instruments, Inc., Foster City, Calif.). Single fluorescent bands were visible on both the nitrocellulose and PEI-coated laminate, indicating that the biotinylated albumin had been successfully blotted from the gel and could still be recognized by the appropriate antibody.

Example 3

Passive Blotting of an Oligonucleotide onto PEI-coated Shrink Film

A Fluorescein isothiocyanate (FITC)-labeled oligonucleotide (5'-FITCAGGATTCCGGGTTAT available from Sigma Genosys, The Woodlands, Tex.) was dissolved in deionized water at concentrations of 56 $\mu$M, 111 $\mu$M, 222 $\mu$M and 445 $\mu$M. 20 $\mu$l of each of these solutions was mixed with 20 $\mu$l of a reducing buffer containing 12 ml Laemmli reagent (Bio-Rad, Hercules, Calif.), 2 ml glycerol, 1 ml 10% sodium dodecyl sulfate, and 0.5 ml 2-mercaptoethanol. Each solution was held at 100° C. for 5 minutes. 10 $\mu$p of the reduced and denatured oligonucleotide solution at each concentration were loaded onto a 4–15% acrylamide gradient pre-cast electrophoresis gel (Bio-Rad). The gel was electrophoresed for 30 minutes at a constant voltage of 100 volts with an initial current of 52 mA and a final current of 31 mA. The gel was then taken out of the precasting cassette and washed with distilled and deionized water. Precut filter papers were soaked in 48 mM tris, 39 mM glycine buffer solution at pH 9.2. Shrink film coated with DMA-VDM copolymer was prepared as in Example 2. The coated shrink film was overcoated by immersing it into a 3% solution of PEI for ten minutes. The coated film was then removed from the PEI solution, rinsed with water and allowed to dry. The dried coated and overcoated film was then placed active side up on a piece of soaked filter paper. The gel was placed over the film and was oriented with the most dilute concentration of oligonucleotide close to a cut corner on the film. A second piece of soaked filter paper was placed on the gel and given liberal amounts of the same buffer used to soak the filter paper. The blot sandwich was pressed together to remove air bubbles and was placed in aluminum foil for passive blotting. After 200 minutes the sandwich was taken apart and the films were viewed over 365 nm UV light. Significant fluorescence was observed on the PEI-coated azlactone shrink film. This results from the transfer of FITC-labeled oligonucleotide from the gel to the film.

Example 4

Passive Blotting of a Protein onto PEI-coated Shrink Film 1 mg/ml FITC-Protein A and 0.5 mg/ml FITC-Goat IgG (both from Sigma Chemical Company, St. Louis, Mo.), both in phosphate buffer (pH 7.5), were mixed 1:1 with reducing buffer containing 12 ml Laemmli reagent, 2 ml glycerol, 1 ml 10% sodium dodecylsulfate (SDS) and 0.5 ml 2-mercaptoethanol. The solution was held at 100° C. for 5 minutes. 30 $\mu$l of each solution were pipetted into each of two 4–15% acrylamide gradient pre-cast electrophoresis gels. The gels were electrophoresed for 15 minutes at a constant voltage of 100 volts and an initial current of 51 mA and a final current of 42 mA. The gel cassettes were opened and the gels rinsed in distilled and deionized water. Precut filter papers were soaked in 48 mM tris, 39 mM glycine buffer at pH 9.2. A DMA-VDM coated shrink film overcoated with 3% PEI (see Example 3) was placed on one filter paper, the gel placed on top of that, and a second filter paper was placed on that to form a sandwich, and the sandwich was pressed to remove air bubbles. The sandwich was allowed to passively blot overnight in aluminum foil at ambient temperature. The next day the blot sandwich was disassembled and visualized over 365 nm ultraviolet light. Faint bands were observed on the film, which corresponded to both the FITC-protein A and the FITC-IgG.

Example 5

Electroblotting of Protein onto Carboxylated Shrink Film

A 1 mg/ml solution of biotinylated albumin (Sigma Chemical Co.) was prepared in 0.1M phosphate-buffered saline, pH 7.5, containing 0.1% bovine serum albumin (PBS-BSA, also available from Sigma Chemical Co.). The conjugate contained nine moles biotin per mole of albumin. Immediately prior to electrophoresis a sample of the biotinylated protein was reduced and denatured with Laemmli reagent (Bio-Rad Corp., Hercules, Calif.) using standard techniques and electrophoresed through a 4–15% acrylamide gradient precast gel (also available from Bio-Rad Corp.) at a constant voltage of 100 volts for 45 minutes.

Shrink film, coated with DMA-VDM described in Example 2 was immersed for fifteen minutes in 0.1N sodium hydroxide solution to produce a film with sodium carboxylate groups on the surface. The film was removed from the sodium hydroxide solution, rinsed with distilled and deionized water and allowed to dry.

The gel was subjected to blotting on the shrink film treated with sodium hydroxide. The treated shrink film was loaded with the treated surface facing the gel. Semi-dry blotting was performed using a Model SD semi-dry electrophoretic transfer cell (Bio-Rad Corp.) according to the package insert instructions. The blotted membranes were blocked overnight at room temperature in a buffer of PBS-BSA containing 1.5% additional bovine serum albumin and 0.1% TWEEN 20 detergent (Bio-Rad Corp.).

To detect the protein on the gel a 1:200 dilution of Cy3-labeled mouse monoclonal anti-biotin antibody (Sigma Chemical Co., 500 μg/ml) was prepared in PBS-BSA. The membranes were incubated in the antibody solution for two hours at room temperature. At the end of the incubation the membranes were washed with a solution of PBS-BSA and 0.1% TWEEN 20 detergent three times for five minutes each on a shaker. The membranes were transferred to a dry surface and stored in the dark. Fluorescent scanning of the membrane was performed using a GENE PIX 4000A array scanner (Axon Instruments, Inc., Foster City, Calif.) at 532 nm. A single fluorescent band was visible on the sodium carboxylate membrane indicating that the biotinylated albumin had been successfully blotted from the gel and could still be recognized by the appropriate antibody.

Example 6

Electroblotting of a Protein onto Dextran Sulfate-coated Shrink Film 1 mg/ml solution of FITC conjugated goat IgG (obtained from Sigma Chemical Co., St. Louis, Mo.) was prepared in a 0.1M phosphate-buffered saline, pH 7.5, containing 0.1% bovine serum albumin (PBS-BSA). The conjugate contained approximately 3 moles FITC per mole of protein. Immediately prior to electrophoresis a sample of the labeled protein was reduced and denatured with Laemmli reagent (Bio-Rad Corp, Hercules, Calif.) using standard techniques. Electrophoresis was performed on this solution using a 4–15% gradient precast acrylamide gel (Bio-Rad Corp.) at a constant voltage of 200 volts for 45 minutes.

Shrink film coated with DMA-VDM was prepared as described in Example 2. This film was immersed for ten minutes in a solution of PEI diluted to 6.0% (w/v) with water. The film was removed from the PEI solution, rinsed with water, and allowed to dry. The PEI-coated film was then immersed in a solution of 0.03% dextran sulfate (Sigma Chemical Co.) in pH 3.9 citrate buffer (52 mM citric acid monohydrate, 154 mM sodium chloride) for five minutes. The film was removed and allowed to dry.

The gel was subjected to blotting on the shrink film coated with dextran sulfate (DS). The coated shrink film was loaded with the DS surface facing the gel. Semi-dry blotting was performed using a Bio-Rad semi-dry electrophoretic transfer cell (Model SD cell) according to the package insert instructions. Fluorescence was visible on the blot when it was visually examined on a 365 nm ultraviolet light table. The blot was also scanned using a GENE PIX 4000A array reader (Axon Instruments, Inc., Foster City, Calif.) at 532 nm. The IgG bands were visible on the blot.

Example 7

Electroblotting of Protein onto PEI-coated Nitrocellulose Shrink Film 1 mg/ml FITC-BSA and 1 mg/ml FITC-IgG solutions were prepared in 10 mM carbonate buffer, pH 9.0. The proteins were mixed 1:1 with cracking solution (12 mls Laemmli reagent, 2 ml glycerol, 1 ml 2-mercaptoethanol, 1 ml 10% SDS) and the solution was held at 100° C. for 5 minutes. The reduced and denatured protein solutions were run on gradient Bio-Rad ready gels (4–15% acrylamide gradient pre-cast electrophoresis gels) for 45 minutes at 100 volts with an initial current of 62 mA and a final current of 32 mA. Following electrophoresis the gels were washed in distilled water for 5 minutes with shaking.

Nitrocellulose-coated shrink film was prepared by dissolving cellulose nitrate (Aldrich Chemical Co., Milwaukee, Wis.) in methyl ethyl ketone to form a 0.75% solution. This solution was coated onto 0.36 OD Ti coated shrink film (reported in International Application No. WO 01/16370) and allowed to dry. The dried shrink film was then dipped for 30 minutes into a 6% solution of PEI in water at ambient temperature after which is was removed from the solution and allowed to dry.

Two filter papers immersed in 0.1 mM carbonate buffer at pH 9.0 were placed on the stage of a Bio-Rad TRANSBLOT semi-dry blotting apparatus. The first filter paper was covered with the nitrocellulose-PEI film and the second filter paper was covered with a piece of Bio-Rad IMMUNO-BLOT PVDF membrane (0.2 μm pore size). One gel was placed on the PVDF, the other on the PEI-coated film. A second piece of filter paper immersed in carbonate buffer 0.1 mM at pH 9.0 was placed over both gels. The sandwich was pressed flat with a roller using hand pressure and the blotting apparatus was assembled for electroblotting. Blots were run for one hour at approximately 30 mA at a constant voltage of 20 volts. Following the blot, films were allowed to dry 15 minutes before observation over a 365 nm UV light box. The nitrocellulose-PEI-coated shrink film showed a visible signal with nondiscrete bands at 365 nm, the PVDF showed visible signal and discrete bands at 365 nm.

The complete disclosures of the patents, patent documents and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A laminate comprising:

a substrate comprising a polymeric film or a relaxed elastomeric material; and a polymeric coating disposed on the substrate over substantially all of the topographical surface area of the laminate and comprising an ionic surface and one or more layers;

wherein at least one layer comprises at least one polymer made from 2-vinylpyridine, 3-vinylpyridine, 4-vinylpyridine, (3-acrylamidopropyl) trimethylammonium chloride, 2-diethylaminoethyl acrylate, 2-diethylaminoethyl methacrylate, 3-dimethylaminopropyl acrylate, 3-dimethylaminopropyl methacrylate, 2-aminoethyl methacrylate, dimethylaminoethyl acrylate, dimethylaminoethyl methacrylate, 2-acryloxyethyltrimethylammonium chloride, diallyldimethylammonium chloride, 2-methacryloxyethyltrimethylammonium chloride, 3-methacryloxy-2-hydroxypropyltrimethylammonium chloride, 3-aminopropylmethacrylamide, dimethylaminoethyl methacrylamide, dimethylaminopropyl acrylamide, 4-vinylbenzyltrimethylammonium chloride, 4-vinyl-1-methylpyridinium bromide, lysine, allylamine, vinylamine, nylons, chitosan, or any combination thereof, and wherein the laminate has a projected surface area and a topographical surface area wherein the topographical surface area is at least about five times greater than the projected surface area.

2. The laminate of claim 1 further comprising a mask layer between the substrate and the polymeric coating.

3. The laminate of claim 1 further comprising a mask layer in direct contact with the substrate.

4. The laminate of claim 1 wherein the coating has a thickness from about 100 Å to about 50 μm.

5. The laminate of claim 4 wherein the coating has a thickness from about 100 Å to about 30 μm.

6. The laminate of claim 5 wherein the coating has a thickness from about 100 Å to about 20 μm.

7. The method of claim 1 wherein at least one layer comprises an amphoteric polymer.

8. A composition comprising:

the laminate of claim 1; and one or more sample molecules affixed to the polymeric coating.

9. The composition of claim 8 wherein at least one sample molecule is a polypeptide, a polynucleotide, a polysaccharide, or any combination thereof.

10. The laminate of claim 1 wherein laminate comprises an undulated surface.

11. The laminate of claim 1 wherein the topographical surface area is at least fifteen times greater the projected surface area.

12. A laminate comprising:

a substrate comprising a relaxed oriented film or a relaxed elastomeric material; and a polymeric coating disposed on the substrate over substantially all of the topographical surface area of the laminate and comprising an ionic surface and one or more layers;

wherein at least one layer comprises at least one polymer made from acrylic acid, methacrylic acid, maleic acid, fumaric acid, itaconic acid, vinylbenzoic acid, N-acryloylamino acid, N-methacryloylamino acid, 2-carboxyethyl acrylate, vinyl phosphoric acid, vinyl phosphonic acid, monoacryloxyethyl phosphate, sulfoethyl methacrylate, sulfopropyl methacrylate, 3-sulfopropyldimethyl-3-methacrylamidopropyl-ammonium inner salt, styrenesulfonic acid, 2-acrylamido-2-methyl-1-propanesulfonic acid, a sulfonated polysaccharide, a carboxylated polysaccharide, or any combination thereof, and wherein the laminate has a projected surface area and a topographical surface area wherein the topographical surface area is at least about five times greater than the projected surface area.

13. The laminate of claim 12 wherein the sulfonated polysaccharide is heparin, dermatan sulfate, or dextran sulfate.

14. The laminate of claim 12 wherein the carboxylated polysaccharide is iduronic acid, carboxymethylcellulose, or alginic acid.

15. A composition comprising:

the laminate of claim 12; and one or more sample molecules affixed to the polymeric coating.

16. The composition of claim 15 wherein at least one sample molecule is a polypeptide, a polynucleotide, a polysaccharide, or any combination thereof.

17. A laminate comprising:

a substrate comprising a relaxed oriented film or a relaxed elastomeric material;

a hydrogel disposed on the substrate; and a coating disposed on the hydrogel over substantially all of the topographical surface area of the laminate, the coating comprising an anionic surface and one or more layers, and wherein the laminate has a projected surface area and a topographical surface area wherein the topographical surface area is at least about five times greater than the projected surface area.

18. The laminate of claim 17 wherein at least one layer comprises polymers made from acrylic acid, methacrylic acid, maleic acid, fumaric acid, itaconic acid, vinylbenzoic acid, N-acryloylamino acid, N-methacryloylamino acid, 2-carboxyethyl acrylate, vinyl phosphoric acid, vinyl phosphonic acid, monoacryloxyethyl phosphate, sulfoethyl methacrylate, sulfopropyl methacrylate, 3-sulfopropyldimethyl-3-methacrylamidopropylammonium inner salt, styrenesulfonic acid, 2-acrylamido-2-methyl-1-propanesulfonic acid, carboxylated polyvinylchloride, a sulfonated polysaccharide, a carboxylated polysaccharide, or any combination thereof.

19. The laminate of claim 18 wherein the sulfonated polysaccharide is heparin, dermatan sulfate, or dextran sulfate.

20. The laminate of claim 18 wherein the carboxylated polysaccharide is iduronic acid, carboxymethylcellulose, or alginic acid.

21. The laminate of claim 17 wherein the hydrogel comprises one or more linking agents.

22. The laminate of claim 21 wherein the linking agents comprise azlactone copolymers.

23. A composition comprising:
    the laminate of claim 16; and
    one or more sample molecules affixed to the coating.

24. The composition of claim 23 wherein at least one sample molecule is a polypeptide, a polynucleotide, a polysaccharide, or any combination thereof.

25. A laminate comprising:
    a substrate comprising a relaxed oriented film or a relaxed elastomeric material;
    a hydrogel disposed on the substrate; and
    a coating disposed on the hydrogel over substantially all of the topographical surface area of the laminate, the coating comprising a cationic surface and one or more layers;
    wherein at least one layer comprises at least one polymer made from 2-vinylpyridine, 3-vinylpyridine, 4-vinylpyridine, (3-acrylamidopropyl) trimethylammonium chloride, 2-diethylaminoethyl acrylate, 2-diethylaminoethyl methacrylate, 3-dimethylaminopropyl acrylate, 3-dimethylaminopropyl methacrylate, 2-aminoethyl methacrylate, dimethylaminoethyl acrylate, dimethylaminoethyl methacrylate, 2-acryloxyethyltrimethylammonium chloride, diallyldimethylammonium chloride, 2-methacryloxyethyltrimethylammonium chloride, 3-methacryloxy-2-hydroxypropyltrimethylammonium chloride, 3-aminopropylmethacrylamide, dimethylaminoethyl methacrylamide, dimethylaminopropyl acrylamide, 4-vinylbenzyltrimethylammonium chloride, 4-vinyl-1-methylpyridinium bromide, lysine, allylamine, vinylamine, nylons, chitosan, or any combination thereof, and
    wherein the laminate has a projected surface area and a topographical surface area wherein the topographical surface area is at least about five times greater than the projected surface area.

26. The laminate of claim 25 wherein the hydrogel comprises one or more linking agents.

27. A laminate having a projected surface area and a topographical surface area wherein the topographical surface area is greater than the projected surface area, and comprising:
    a substrate comprising a polymeric film;
    a hydrogel disposed on the substrate, wherein the hydrogel comprises one or more linking agents, and wherein the linking agents comprise azlactone copolymers; and
    a coating disposed on the hydrogel over substantially all of the topographical surface area of the laminate, the coating comprising a cationic surface and one or more layers;
    wherein at least one layer comprises at least one polymer made from 2-vinylpyridine, 3-vinylpyridine, 4-vinylpyridine, (3-acrylamidopropyl) trimethylammonium chloride, 2-diethylaminoethyl acrylate, 2-diethylaminoethyl methacrylate, 3-dimethylaminopropyl acrylate, 3-dimethylaminopropyl methacrylate, 2-aminoethyl methacrylate, dimethylaminoethyl acrylate, dimethylaminoethyl methacrylate, 2-acryloxyethyltrimethylammonium chloride, diallyldimethylammonium chloride, 2-methacryloxyethyltrimethylammonium chloride, 3-methacryloxy-2-hydroxypropyltrimethylammonium chloride, 3-aminopropylmethacrylamide, dimethylaminoethyl methacrylamide, dimethylaminopropyl acrylamide, 4-vinylbenzyltrimethylammonium chloride, 4-vinyl-1-methylpyridinium bromide, lysine, allylamine, vinylamine, nylons, chitosan, or any combination thereof.

28. A composition comprising:
    the laminate of claim 25; and
    one or more sample molecules affixed to the coating.

29. The composition of claim 28 wherein at least one sample molecule is a polypeptide, a polynucleotide, a polysaccharide, or any combination thereof.

30. A laminate comprising:
    a substrate comprising a relaxed oriented film or a relaxed elastomeric material;
    a hydrogel comprising at least one linking agent disposed on the substrate; and one or more bifunctional ionic molecules covalently linked to at least one linking agent, and
    wherein the laminate has a projected surface area and a topographical surface area wherein the topographical surface area is at least about five times greater than the projected surface area.

31. The laminate of claim 30 wherein at least one bifunctional ionic molecule is an aminocarboxylic acid, an aminosulfonic acid, an aminophosphonic acid, an aminophosphoric acid, or a polyamine.

32. A composition comprising:
    the laminate of claim 30; and one or more sample molecules affixed to the one or more bifunctional ionic molecules.

33. The composition of claim 32 wherein at least one sample molecule is a polypeptide, a polynucleotide, a polysaccharide, or any combination thereof.

34. A laminate comprising:
    a substrate comprising a relaxed oriented film or a relaxed elastomeric material;
    a hydrogel disposed on the substrate and comprising one or more hydrolyzed azlactone moieties, and
    wherein the laminate has a projected surface area and a topographical surface area wherein the topographical surface area is at least about five times greater than the projected surface area.

35. A composition comprising:
    the laminate of claim 34; and
    one or more sample molecules affixed to one or more hydrolyzed azlactone moieties.

36. The composition of claim 31 wherein at least one sample molecule is a polypeptide, a polynucleotide, a polysaccharide, or any combination thereof.

37. A laminate comprising:
    a substrate comprising a relaxed oriented film or a relaxed elastomeric material;
    a polymeric coating disposed on the substrate over substantially all of the topographical surface area of the laminate and comprising an ionic surface and one or more layers;
    wherein at least one layer comprises at least one polymer made from 2-vinylpyridine, 3-vinylpyridine, 4-vinylpyridine, (3-acrylamidopropyl) trimethylammonium chloride, 2-diethylaminoethyl acrylate, 2-diethylaminoethyl methacrylate, 3-dimethylaminopropyl acrylate, 3-dimethylaminopropyl methacrylate, 2-aminoethyl methacrylate, dimethylaminoethyl acrylate, dimethylaminoethyl methacrylate, 2-acryloxyethyltrimethylammonium chloride, diallyldimethylammonium chloride, 2-methacryloxyethyltrimethylammonium chloride, 3-methacryloxy-2-hydroxypropyltrimethylammonium chloride, 3-aminopropylmethacrylamide, dimethylaminoethyl methacrylamide, dimethylaminopropyl acrylamide, 4-vinyl-1-methylpyridinium bromide, lysine, allylamine, vinylamine, nylons, chitosan, or any combination thereof, and wherein the laminate has a projected surface area and a topographical surface area wherein the topographical surface area is at least about five times greater than the projected surface area.

* * * * *

UNITED STATES PATENT AND TRADEMARK OFFICE
CERTIFICATE OF CORRECTION

PATENT NO. : 6,783,838 B2
DATED : August 31, 2004
INVENTOR(S) : Coleman, Patrick L.

It is certified that error appears in the above-identified patent and that said Letters Patent is hereby corrected as shown below:

Column 6,
Line 47, delete "nitrites" and insert -- nitriles --, therefor.

Column 17,
Line 14, delete "polymeric" and insert -- relaxed oriented --, therefor.
Lines 55 and 60, delete "composition" and insert -- composite --, therefor.

Column 18,
Line 30, delete "composition" and insert -- composite --, therefor.

Column 19,
Lines 5 and 8, "composition" and insert -- composite --, therefor.

Column 20,
Lines 8, 12, 31, 35, 48 and 52, delete "composition" and insert -- composite --, therefor.
Line 58, after "material;" insert -- and --.

Signed and Sealed this

Seventh Day of December, 2004

JON W. DUDAS
*Director of the United States Patent and Trademark Office*